(12) United States Patent
Weitzel et al.

(10) Patent No.: US 6,551,397 B2
(45) Date of Patent: Apr. 22, 2003

(54) PIGMENT PREPARATION

(75) Inventors: Joachim Weitzel, Savannah, GA (US); Wolfgang Hechler, Lautertal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/133,415

(22) Filed: Apr. 29, 2002

(65) Prior Publication Data

US 2002/0157574 A1 Oct. 31, 2002

(30) Foreign Application Priority Data

Apr. 27, 2001 (DE) .......................... 101 20 856

(51) Int. Cl.$^7$ ............................... C04B 14/00
(52) U.S. Cl. ................ 106/479; 106/415; 106/417; 106/418; 106/474; 106/502
(58) Field of Search .................. 106/415, 417, 106/418, 474, 479, 502

(56) References Cited

U.S. PATENT DOCUMENTS 5,672,200 A * 9/1997 Heinz et al. ................ 106/403
6,488,756 B1 * 12/2002 Schoen et al. .............. 106/415

* cited by examiner

*Primary Examiner*—C. Melissa Koslow
*Assistant Examiner*—Shalie Manlove
(74) *Attorney, Agent, or Firm*—Millen, White, Zelano & Branigan, P.C.

(57) ABSTRACT

The present invention relates to a pigment preparation comprising BiOCl pigments, one or more luster pigments and spherical particles, and to the use thereof in printing inks, security printing inks, surface coatings, paints, plastics and in cosmetic formulations.

11 Claims, No Drawings

PIGMENT PREPARATION

The present invention relates to a pigment preparation essentially consisting of a mixture of BiOCl pigments, luster pigments and spherical particles, and to the use thereof, in particular in printing inks.

Printing inks generally consist of binders, pigments or dyes and additives. In print products for packing prints, labels and high-quality magazines, the requirement to provide a special luster on the imaged articles occurs ever more frequently.

Offset printing inks comprising luster pigments all exhibit the disadvantage that they have problems with production run stability. They tend to build up or sediment rapidly on the inking system, printing plate and rubber blanket, meaning that a problem-free production run of more than 10,000 sheets is generally impossible. A fundamental problem is the strong tendency of luster pigments, in particular pearlescent pigments, due to the platelet-shaped structure and the specific chemical/physical surface properties, to form agglomerates in the printing ink, in which the pigments lie one on top of the other in the manner of a stack and can only be separated with difficulty owing to strong adhesion. Furthermore, the provision of luster on such proofs is generally unsatisfactory, which is attributable to the inadequate amount of pigments transferred to the print product. The ink becomes depleted in pigment on the transport route via inking system, plate and rubber blanket. The pigment accumulates at exposed points on the plate and blanket and results in piling-up.

Pigment preparations comprising pearlescent pigments and spherical particles have already been disclosed in DE-A-4446456. The use of BiOCl pigments in printing inks is described in publications by EM Industries and Mearl Corporation. Preparations comprising pearlescent pigments for offset printing have high luster, but have the disadvantage that the pearlescent pigments exhibit a strong tendency to migrate into the damping solution during printing, depending on the binder used. BiOCl pigments are ground during the printing process, which has the consequence that the optical properties of the pigments are substantially lost.

An object was therefore to provide a pigment preparation, preferably for printing inks, in particular for offset printing inks, which comprises luster pigments, but does not have the above-mentioned disadvantages.

Surprisingly, it has now been found that less pigment migration into the damping solution is observed and the quality of the luster effect and the amount of transferred pigment particles in the printing ink can be increased if a pigment preparation is used which, besides luster pigments, additionally comprises BiOCl pigments and spherical particles.

The pigment preparation according to the invention has the following advantages over the offset preparations from the prior art which comprise only pearlescent pigments or only BiOCl pigments:

higher luster
a more closed print image
better pigment transfer
less pigment migration into the damping solution
better hiding power.

The invention thus relates to a pigment preparation comprising BiOCl pigments, one or more luster pigments, spherical particles and, if desired, additives from the printing sector.

Due to the combination of BiOCl pigments with luster pigments, significantly more coloristic effects can be achieved in the printing inks. The ratio between BiOCl and luster pigment is preferably from 99:1 to 1:99 and in particular from 70:30 to 30:70. The pigment preparation according to the invention preferably comprises from 40 to 99.8% by weight, in particular from 70 to 99.5% by weight, of BiOCl and luster pigments, based on the preparation.

BiOCl pigments for offset printing are commercially available, for example from Engelhard under the name Mearlite Ultra Fine OFS and from Merck KGaA under the name Bi-Flair® 66a. The commercially available BiOCl pigments have particle sizes of 1–50 $\mu$m. For the pigment preparation according to the invention, BiOCl pigments having particle sizes of 5–20 $\mu$m are particularly suitable.

The BiOCl pigments can also be employed in the pigment preparation according to the invention in paste form. Compared with pulverulent BiOCl pigments, these dispersions have significantly higher silver luster, higher transparency and are even easier to disperse. Particularly suitable are BiOCl pastes in castor oil, nitrocellulose, mineral oil and alkyd resin.

A further important constituent of the pigment preparation according to the invention is the luster pigment. The pigment preparation may also comprise a mixture of different luster pigments, in order, for example, to achieve certain color effects.

The luster pigments used are preferably pigments based on platelet-shaped, transparent or semi-transparent substrates of, for example, phyllosilicates, such as, for example, mica, synthetic mica, $SiO_2$ platelets, glass platelets, $TiO_2$ platelets, $Al_2O_3$ platelets, talc, sericite, kaolin, of glass or other silicate materials which are covered with rare-earth metal sulfides, such as, for example, $Ce_2S_3$, with colored or colorless metal oxides, such as, for example, $TiO_2$, titanium suboxides, titanium oxynitrides, pseudobrookite, $Fe_2O_3$, $Fe_3O_4$, $SnO_2$, $Cr_2O_3$, ZnO, CuO, NiO and other metal oxides, alone or in a mixture, in a uniform layer or in successive layers (multilayer pigments). Pearlescent pigments are disclosed, for example, in the German patents and patent applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are commercially available, for example under the trade name Iriodin® from Merck KGaA, Darmstadt, Germany.

Particularly preferred pigment preparations comprise $TiO_2$-, $Fe_2O_3$ or $TiO_2/Fe_2O_3$-coated mica, $Al_2O_3$, glass or $SiO_2$ platelets. The $SiO_2$ platelets can be coated, for example, as described in WO 93/08237 (wet-chemical coating) or DE-A 196 14 637 (CVD process). $Al_2O_3$ platelets are disclosed, for example, in EP 0 763 573 A1. Platelet-shaped substrates which are covered with one or more rare-earth metal sulfides are disclosed, for example, in DE-A 198 10 317.

Also suitable are metal-effect pigments, in particular aluminium platelets modified for water-based or solvent-containing systems, as marketed by Eckart under the trade name Rotovario Aqua® or Stapa Hydroxal® for water-based applications, and Variocrom® and Paliocrom® pigments from BASF, in particular also those from EP-A 0 681 009 A1, EP-A 0 632 110 A1 and EP-A 0 634 458 A1, and LCP (liquid crystal polymer) pigments. Likewise suitable are all holographic pigments and platelet-shaped pigments with metal layers which are known to the person skilled in the art. Pigments of this type are marketed by Flex, BASF, Eckart and Schlenk.

The pigment preparations according to the invention may comprise one or more luster pigments, with it frequently being possible to achieve particular color and luster effects through the use of at least two different luster pigments.

In addition to the pearlescent pigments and BiOCl pigments, the pigment preparation according to the invention may also comprise carbon black particles, fluorescent pigments and/or organic colored pigments. The preparation then preferably consists of 50–100% by weight of BiOCl and luster pigments and 0–50% by weight of carbon black particles, fluorescent pigments and/or colored pigments. However, the content of all pigments in the pigment preparation should preferably not exceed 99.4% by weight. Furthermore, it is possible to add substances and particles which enable product identification (tracers).

The use of spherical particles in offset printing inks has already been disclosed in JP 62-143 984. The spherical resin or wax particles described therein, having a content of 0.1–20% by weight in the printing ink, which comprise neither luster pigments nor BiOCl pigments, are stirred in in order to improve the build-up properties and to prevent picking of the paper by the rubber blanket.

Suitable spherical materials are, in particular, hollow glass, wax or polymer beads made from vinyl resins, nylon, silicone, epoxy resins, olefin resins, polystyrenes and inorganic materials, such as, for example, $TiO_2$, $SiO_2$ or $ZrO_2$. Preference is given to the use of hollow beads, furthermore also solid beads, having a particle size of from 0.05 to 150 µm. Particular preference is given to the use of hollow glass, wax or polymer beads in the pigment preparation according to the invention.

The spherical particles have a particle size of 0.05–150 µm, preferably 0.05–50 µm, and in particular 1–30 µm. Spherical particles based on $SiO_2$ in a particle size range of 3–10 µm are known, for example, as materials for high-pressure liquid chromatography and are marketed, for example, as LiChrospher® by Merck KGaA, Darmstadt. These materials are preferably employed in monodisperse form, i.e. with the most uniform particle size possible. Monodisperse spherical particles of this type based on $SiO_2$, $TiO_2$ and $ZrO_2$ are known. Monodisperse $SiO_2$ can be prepared, for example, as described in DE 36 16 133. Hollow glass beads are marketed, for example, under the trade name Q-CEL by PQ Corporation, USA, or Scotchlite by 3M, Frankfurt, Germany.

The improved deagglomeration of the BiOCl and luster pigments in a printing ink is evident even with small amounts of spherical particles in the pigment preparation. Thus, even at a content of only 0.5% by weight of spherical particles, based on the pigment preparation, significantly improved production run properties are evident in the printing inks which comprise the pigment preparation according to the invention. In general, pigment preparations having a content of 1–10% by weight, in particular 15% by weight, of spherical particles are used.

In the pigment preparation according to the invention, the spherical particles prevent the platelet-shaped BiOCl and luster pigments from lying one on top of the other to a significant extent and thus being able to exert strong adhesion. As electron photomicrographs show, the spherical particles accumulate at the surface of the platelet-shaped luster pigment and therefore facilitate, like a type of ball bearing, easy mobility of the pigment platelets against one another in the printing ink, thus substantially suppressing piling-up of the pigments during the printing process.

On use of the pigment preparation according to the invention in printing inks, the spherical particles can "shatter" pre-existing pigment agglomerates through the spherical particles being forced into the pigment clusters during the printing process and "blowing up" these agglomerates. The larger spherical particles may be partly destroyed in the process. Preferably, only particles having a relatively small particle diameter are found in the print product, while the fragments have a loosening effect in the pigment agglomerate.

As a further constituent, the pigment preparation according to the invention can comprise a phosphate derivative in amounts of 0.1–5% by weight, preferably 1–3% by weight, based on the pigment preparation. Suitable phosphate derivatives are, for example, higher and lower metapolyphosphates and pyrophosphates. Particular preference is given to alkali metal polyphosphates, in particular sodium polyphosphate.

It is frequently advisable additionally to stir a dispersant into the pigment preparation. All dispersants known to the person skilled in the art can be used, for example as described in Karsten, Lackrohstofftabellen [Tables of Raw Materials for Surface Coatings], 9th Edition, 1992. Particularly suitable are dispersants based on polyacrylates or polymethacrylates. The amount of dispersant employed should not be more than 10% by weight, preferably 0.05–5% by weight, based on the finished printing ink.

Production of the pigment preparation is simple and easy to handle. Firstly, the luster pigment is mixed vigorously with the spherical particles by shaking or in a dry mixer. This is followed by addition of the phosphate derivative and the BiOCl pigments, which are either stirred in as powders or are added in the form of a dispersion consisting of salt and a liquid component. Suitable liquid components are, in particular, mineral oils or other non-drying oils, furthermore drying oils, such as, for example, linseed oil, soya oil, as well as water or organic solvents. The liquid component should then make up a maximum of 10% by weight, based on the pigment preparation. The pigment preparation can also be produced by simultaneously introducing all components and then mixing them vigorously with one another. The finished pigment preparation can then be admixed with formulations, such as, for example, printing inks, surface coatings, paints, plastics and cosmetic preparations.

The pigment preparation according to the invention is particularly suitable for the pigmenting of printing inks. Pigmented printing inks of this type can be employed for all known printing methods, in particular for offset printing, furthermore letterpress printing, letterset, gravure printing, flexographic printing and screen printing, furthermore for overprint varnishing and for coatings. They are preferably used for offset printing. It can be used both for roll offset printing and for sheet-fed offset printing by the dry or wet method; however, they are particularly suitable for sheet-fed offset printing by the wet method.

The pigment preparation according to the invention is then dispersed in the printing ink or in the binder with the aid of a stirrer unit with propeller or paddle stirrer, if desired at different dispersion temperatures. The pigment particles are coated by the binder in the process.

For the preparation of a pigmented printing ink, in particular an offset printing ink, all commercially available binders can be used. Binders of this type consist of known synthetic or natural resins, optionally drying oils, mineral oils and additives, as described, for example, in Karsten, Lackrohstofftabellen [Tables of Raw Materials for Surface Coatings], 9th Edition, 1992. The resins used preferably have a relatively low melt or solvent viscosity. However, it is also possible for highly polymerized and highly viscous components to be present. Combinations of hard resins and alkyd resins have proven particularly suitable since these wet the pigments better and give more lustrous and abrasion-resistant prints. In particular, use is made of binders which are composed of 50–90% by weight of hard resin and 550% by weight of alkyd resin. The hard resins used are preferably hydrocarbon resins. The hydrocarbon resins used can have an acid number close to 0 mg of KOH/g of substance, but they may also have been modified and have acid numbers of up to 30 mg of KOH/g of substance. Furthermore, the binder may comprise 1–50% by weight of a mineral oil. The ink components are matched to one another in such a way that a stable ink/water balance which is suitable for relatively low ink viscosities is achieved.

The printing ink is dried by oxidative polymerization of the resins and by means of oils, such as, for example, linseed oil, wood oil or castor oil, which are absorbed into the paper during printing. The drying process can be further accelerated by additives of drying catalysts (siccatives), usually fatty acid salts of cobalt, lead, manganese, etc. The proportion of drying oils in the offset printing inks according to the invention is in the range 0–50% by weight, preferably 0–30% by weight. Further additives may be incorporated into the printing ink in order to modify the ink properties for specific applications. These additives may be wax compounds, drying agents, dispersants, solvents, thickeners, lubricants, pigment fillers and/or antioxidants. Further details on the basic properties of offset printing inks are given in A. Rosenberg, Der Polygraph (11), 1153 (1987) and B. Grande, Coating (4), 138 (1987).

The very low-viscosity pigment-containing printing inks frequently do not produce adequate dot sharpness. However, this is necessary, particularly in fine screens, in order to prevent clogging of the print. It is therefore recommended to provide the printing ink with structure. Thus, the addition of a structure former may sufficiently improve the dot sharpness. The pigment preparation according to the invention then preferably comprises 0.1–3% by weight of a structure former. Besides the improved dot sharpness, a pigment preparation modified in this way exhibits significantly better pigment transfer, better production run properties and an improvement in settling behaviour in a printing ink.

The choice of the resins in the binders and the proportion of BiOCl and luster pigments in the printing ink enable the parameters which are crucial for the printing process, such as dispersibility, tack and viscosity, to be adjusted individually. The viscosity and tack are dependent on one another for the same ink build-up, but can also be changed individually in a targeted manner by means of a special build-up. It should be noted here that printing inks having excessive tack can cause parts of the paper to tear (picking). Inks having inadequate tack are not transferred in a suitable manner during the printing process. If the penetration of the ink is too great, the ink becomes visible on the opposite side of the paper or causes mottling or lack of clarity of the image. Poorly controlled penetration can cause smearing and ink set-off. The printing ink exhibits absolutely no problems with splashing off the inking system rolls, not even at printing speeds of 10,000 sheets per hour.

Printing inks comprising the pigment preparation according to the invention are of particular importance, especially with respect to graphic products in the advertising sector and in the case of high-quality print products, since the finished prints meet the highest aesthetic demands owing to their luster.

In order to improve the printing speeds and production run properties, it is advisable, in particular in the case of offset printing, to use printing blankets having a smooth surface, where the modified surface preferably consists of polyvinyl chloride, polyurethane, polyester or Teflon and should have a surface hardness of about 88–95° Shore. The use of a printing blanket of this type in combination with the pigment preparation according to the invention in the printing ink ensures perfect ink transfer.

The invention thus also relates to printing inks which comprise up to 80% by weight, preferably from 5 to 70% by weight, in particular from 10 to 55% by weight, of the pigment preparation according to the invention.

The pigment preparation according to the invention is distinguished by its high luster and can therefore be employed for a very wide variety of purposes. Besides use in printing inks, including security printing inks, it can furthermore be used in plastics, surface coatings, paints and, owing to the good skin feeling, also in cosmetic preparations. Incorporation of the preparation of the invention in such materials can be made in view of wholly conventional knowledge.

The invention thus also relates to formulations which comprise the pigment preparation according to the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents and publications, cited above or below, and of corresponding German Application No. 10120856.1, filed Apr. 27, 2001, is hereby incorporated by reference.

EXAMPLES

I. Pigment Preparation

Example 1

27 g of Scotchlite S22 from 3M are added to 600.0 g of Iriodin® 123 (pearlescent pigment: $TiO_2$ on mica having a particle size of 5–20 μm from Merck KGaA) and stirred in homogeneously at 300 rpm. The stirrer motor used is a Dispermat AE 6C. A suspension of 28.4 g of sodium polyphosphate finely dispersed in 28.4 g of mineral oil PKWF 28/31 is subsequently prepared and mixed together with 428.6 g of Bi-Flair® 66a (BiOCl pigment having a particle size of 1–20 μm from Merck KGaA). This is added to the Iriodin® 123/Scotchlite mixture. The combination is mixed homogeneously at 650 rpm for 16 minutes.

Example 2

22.5 g of Scotchlite S 22 are added to 600.0 g of Iriodin® 326 (pearlescent pigment: $TiO_2/Fe_2O_3$ on mica having a particle size of 5–25 μm from Merck KGaA) and stirred in homogeneously at 300 rpm. The stirrer motor used is a Dispermat AE 6C. The stirrer used is a propeller stirrer (diameter 16 cm). Two suspensions are subsequently prepared.
1. 22.5 g of sodium polyphosphate are dispersed in 23.7 g of mineral oil using a bead mill.
2. 15.0 g of PV Fast Yellow (Hoechst) are dispersed in 85 g of mineral oil PKWF 28/31, likewise using a bead mill.

The two suspensions are mixed homogeneously with 214 g of Bi-Flair® 66a (pastes of BiOCl pigments in mineral oil) and added to the Iriodin® 326/Scotchlite mixture. The mixture is mixed homogeneously at 650 rpm for 16 minutes.

II. Preparation of an Offset Printing Ink 2.1 489 g of the pigment preparation from Example 1 are stirred into 611 g of Gebr. Schmidt bronze varnish 1 1A1034-1 (Gebr. Schmidt) using a stirrer (diameter 10 cm) at 450 rpm for 20 minutes. The ink can then be printed directly in the printing machine.

2.2 655 g of the pigment preparation from Example 2 are stirred into 845 g of Gebr. Schmidt bronze varnish 11A1034-1 using a stirrer (diameter 10 cm) at 450 rpm for 20 minutes. The ink can then be printed directly in the printing machine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment preparation comprising at least one BiOCl pigment, at least one luster pigment, and spherical particles.

2. The pigment preparation according to claim 1, having a ratio of BiOCl to luster pigment of 99:1 to 1:99.

3. The pigment preparation according to claim 1, wherein the luster pigment is a pearlescent pigment.

4. The pigment preparation according to claim 2, wherein the pearlescent pigment is a mica, $SiO_2$, glass or $Al_2O_3$ platelet covered with at least one metal-oxide layer.

5. The pigment preparation according to claim 1, wherein the spherical particles are glass, wax or $SiO_2$ beads or hollow polymer beads.

6. The pigment preparation according to claim 1, additionally comprising up to 30% by weight of a liquid component.

7. The pigment preparation according to claim 1, additionally comprising a phosphate compound.

8. The pigment preparation according to claim 7, wherein the phosphate derivative is present in an amount of 0.1–5% by weight.

9. A printing ink, security printing ink, surface coating, paint, plastic or cosmetic formulation, comprising a pigment preparation according to claim 1.

10. A printing ink comprising a pigment preparation according to claim 1.

11. An ink according to claim 10, wherein the pigment preparation is present in an amount of up to 80%.

* * * * *